United States Patent [19]

Marsoner et al.

[11] 4,366,040
[45] Dec. 28, 1982

[54] CAPILLARY-REFERENCE ELECTRODE

[75] Inventors: Hermann Marsoner; Christoph Ritter, both of Graz, Austria

[73] Assignee: Hans List, Graz, Austria

[21] Appl. No.: 300,557

[22] Filed: Sep. 9, 1981

[30] Foreign Application Priority Data

Sep. 10, 1980 [AT] Austria ............................... 4562/80
Jul. 8, 1981 [AT] Austria ............................... 3025/81

[51] Int. Cl.³ .......................................... G01N 27/30
[52] U.S. Cl. ............................ 204/195 R; 204/195 F; 128/635
[58] Field of Search ................ 204/195 R, 195 F; 128/635

[56] References Cited

FOREIGN PATENT DOCUMENTS 1047138 11/1966 United Kingdom ............ 204/195 R
2000297  1/1979 United Kingdom ............ 204/195 R

OTHER PUBLICATIONS

Osswald, et al., "Flow-Through System of High Stability for Measurement of Ion Activities in Clinical Chem.", Chimia, vol. 31, 2/1977.

Primary Examiner—G. L. Kaplan
Assistant Examiner—N. Nguyen
Attorney, Agent, or Firm—Watson, Cole, Gridle & Watson

[57] ABSTRACT

In a capillary reference electrode with a capillary body which comprises a measuring chamber connected through an electrolytic bridge to a test sample which is adapted to be introduced into a capillary bore, the inlet orifice for the electrolyte is arranged at a point of the measuring chamber which is in a low position when the element is installed and the outlet orifice is arranged at a high position of the measuring chamber. The electrolytic bridge is formed through a communicating passage which has a substantially conical narrow end adjacent to the capillary bore with a very fine communication bore leading to the capillary bore. The resulting economy in electrolyte-consumption and absence of sensitivity in respect of potentially occuring air bubbles are further improved by providing the said communication bore with a substantially annular cross section.

11 Claims, 8 Drawing Figures

CAPILLARY-REFERENCE ELECTRODE

BACKGROUND OF THE INVENTION

The present invention relates to a capillary reference electrode comprising a capillary body having a measuring chamber connected by an electrolytic bridge with a test-sample capable of being introduced into a capillary bore of the capillary body, and a reference electrode extending into the measuring chamber. The measuring chamber is provided with an inlet and an outlet for charging the measuring chamber with an electrolyte.

DESCRIPTION OF THE PRIOR ART

A device of this kind is known, for example from Austrian Pat. No. 278,710, according to which the measuring chamber is arranged in the switching element of a rotatable three-way valve. This three-way valve affords three operative switching positions: in the first of these the inlet and the outlet opening of the measuring chamber are both closed, in a second position these openings communicate with corresponding passageways for the electrolyte and in a third switching position the inlet opening of the measuring chamber is closed whilst the outlet opening is in communication with a lateral opening in the measuring capillary. In other words, by means of the rotatable switching element the electrolytic bridge between the capillary passage, into which the sample can be introduced, and the measuring chamber of the reference electrode, can be established or broken, as required. The latter facility is particularly needed in this known arrangement to enable the capillaries to be cleaned. Besides the distinct disadvantage of mechanical vulnerability of the rotatable element in this known device there is also the serious drawback of high consumption in electrolyte and an increased risk of dirt penetration to the measuring chamber because this has relatively large dimensions. There is also a risk of air bubbles arising, for example, from temperature changes in the electrolytic solution which are extremely difficult to eliminate in view of the general constructional lay-out of this known device and which can easily block the communication between measuring chamber and test-channel, thus preventing an accurate and reliable measuring operation altogether.

SUMMARY OF THE INVENTION

It is an aim of the present invention to improve a capillary reference electrode of the kind specified in such a way that the abovementioned disadvantages appertaining to known devices are obviated. A further object is that any air bubbles which may form in such an arrangement can be easily, quickly and safely expelled so that they will not affect the measuring operation.

This is achieved, according to the present invention, due to the fact that the electrolyte inlet of the measuring chamber, in the installed state of the capillary body, is arranged in a geometrically low position and the electrolyte outlet at a geometrically high position on the measuring chamber and that for the electrolytic bridge is provided a communicating passage between measuring chamber and capillary bore which communicating passage adjacent to said capillary bore has a substantially conical end with a communication bore, which has a clear flow section corresponding to a bore with a diameter in the range of 0.01 to 0.1 mm, to the capillary bore. Due to this special arrangement of the inlet and outlet for the electrolyte potentially harmful air bubbles which may form in the measuring chamber of the reference electrode are continually evacuated when the device is in use, thus preventing any distortion of measured data. Through the conically tapered communicating passage for the electrolytic bridge leading into the capillary bore, a certain amount of suction pressure is generated in the communicating passage when a test-sample is sucked into the capillary bore, whereby a small amount of electrolytic fluid, depending in quantity on the size of the communication bore at the pointed end of the passage, is sucked into the capillary bore itself with the result that any air bubbles or impurities which may be present in the communicating passage are sucked into the capillary test-channel by the follow-up flow of electrolytic fluid and furthermore, on making contact with the sample precisely that amount of electrolyte is applied to the latter which is required for the actual measuring operation. The whole arrangement requires no mechanically actuated parts or elements of any kind whatsoever and all parts thereof may be of such judiciously chosen dimensions that electrolyte consumption may be confined to a few $\mu l$ for each test-sample. Since the communicating passage and more particularly, the pointed end region thereof adjacent to the capillary communication bore, to the capillary bore is flushed and cleaned out for every electrolyte withdrawal, there is very little danger of soiling and data distortion due to bubbles or impurities in the passage.

According to another feature of this invention a flexible tube connector is provided for connecting the communicating passage to the measuring chamber which latter is arranged externally of the capillary body. This enables a largely free choice in respect of the dimensions of the capillary body because the measuring chamber as well as the electrode projecting into the same are now arranged outside this body.

In some practical applications it is found to be an advantage if—according to another proposal of this invention—the measuring chamber together with the inlet and outlet for the electrolyte is formed within the capillary body itself. Such an arrangement allows the volume of electrolyte in the electrolytic bridge between measuring chamber and capillary bore to be kept to a minimum and the formerly required connections or union parts for connecting the measuring chamber to the electrolytic bridge can be wholly dispensed with.

In a preferred embodiment of the present invention the communicating bore to the capillary bore is provided in a tapered nozzle tip, which is extruded from a polymer material and secured, preferably adhesively fixed, in the communicating passage adjacent to the capillary bore. The communicating passage has a bulbous, preferably pear-shaped expanded region in the vicinity of the communicating bore. This pear-shaped expanded region at the pointed end of the communicating passage was found, in the course of practical experiments, to have the totally unsuspected effect that any parts of the sample which may have penetrated into the communicating passage are retained in this bulbous region which has the effect of a mixing chamber. Since the enlargement in the nozzle tip has a volume of only a few $\mu l$, an adequate flushing and cleaning action is obtained during the next withdrawal of electrolyte, that is to say during the next aspiration of a test sample into the capillary bore. Particularly where polymer flexible tube materials are used for the nozzle tip, such as for example polyethylene or polytetrafluoroethylene, it is virtually impossible for any sample residue to cling to the walls of the bulbous region. Quite unexpectedly such a bulbous region in the nozzle tip is formed quite simply by heating and corresponding drawing-out of a piece of polymer flexible tube material which, under these conditions, tends not to result in a cross sectional reduction but rather in an expansion of the cross section.

In further development of the present invention, with a view to obtaining a situation requiring a minimum of work for cleaning or clearing the communication bore to the capillary bore of any congestion which might occur or, better still, generally avoiding such congestions altogether, a detachable insert with a likewise substantially conical point may be arranged in the region of the conical end of the communicating passage and co-act with the latter to define the capillary bore communication. The advantage of this arrangement resides in that, in the event of a congestion or obstruction in the communicating bore to the capillary bore the said insert element can be easily removed so that cleaning is simple. Another vital advantage resides in that the communication bore which thus is of substantially annular cross sectional configuration, is much less likely to be obstructed by a single impurity than a circular cross sectioned bore of the same cross sectional size, which is altogether extremely favorable with regard to the useful service life of the capillary reference electrode.

According to a further development of this invention the pointed end of the insert element has a smaller angle of conicity than the end of the communicating passage so that the smallest cross sectional dimension of the communicating passage which on the one hand limits flow rate and, on the other hand, takes care of the retention of impurities, is directly at the junction with the capillary bore.

According to another feature proposed by this invention, longitudinally extending V-grooves may be formed in the end cone of the insert element, the number and size of which, either independently of the conical form of the communicating passage and the insert element, or jointly with this configuration, afford a large amount of control in respect of the size and form of the clear cross section of the communication bore to the capillary bore. In accordance with a further proposal of this invention the insert element may be axially adjustable relative to the cone of the communicating passage by means of a screw thread which, besides the earlier described advantages, presents the additional facility of precisely controlling the amount of fluid flow through the communicating passage by exact positioning of the inset element to compensate for any misalignment of the relative positions of the two cones due to manufacturing and assembly tolerances. Apart from this the insert element may also be secured and fitted in the communicating passage in any other convenient fashion, provided always that the free flow through the passage is not unduly obstructed by the fastener means.

According to another feature of the present invention, as applied to an electrode with a capillary body which is substantially disc-shaped, comprises a through-extending axial capillary bore and end faces which are adapted for connection to further identical bodies, a special advantage is obtained if the communicating passage extends in such a way that in the fitted state of the capillary body it is arranged to extend substantially obliquely from above and normal to the capillary bore. Such an arrangement is a particularly simple and safe way of enabling air bubbles which may occur in the electrolytic bridge to rise up into the measuring chamber whence they are continually removed due to the arrangement of the electrolyte inlet and outlet of the measuring chamber according to this invention.

In a measuring system with a capillary reference electrode according to this invention further advantages are obtained if, according to yet another feature of this invention, the electrolyte-inlet and outlet of the measuring chamber are connected to an electrolyte circulation system, which, besides comprising a pump, preferably a peristaltic pump, also includes an electrolyte reservoir and, where required, suitable shut-off valves forwardly of and after the measuring chamber. This reservoir holds a specified quantity of electrolyte fluid which, in view of the very low electrolyte consumption achieved by the present invention, allows, completely without problems, automatic measuring operations to be carried out over a long period of time.

DESCRIPTION OF THE DRAWINGS

The present invention is hereinafter more particularly described with reference to embodiments illustrated by way of example in the accompanying drawings in which.

DESCRIPTION OF THE PREFERRED EMBODIMENTS

Figure 1:
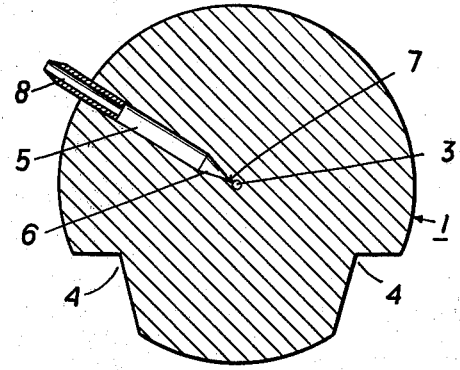
FIG. 1 is a cross sectional view through a capillary body of a reference electrode according to this invention.

The capillary element 1 according to FIG. 1 is substantially disc-shaped, comprising an axially through-extending capillary bore 3 and its end faces are adapted, in a manner not shown, for the connection of further identical elements. On the lower side of the disc-shaped capillary element 1, there are cutouts 4 which facilitate concentric alignment and securing of a plurality of such capillary elements.

For making an electrolytic bridge between the capillary bore 3 or the test-sample which is adapted to be introduced into this bore, and the measuring chamber (not shown) a communicating passage 5 is provided which has a substantially conical point 6 adjacent to the capillary bore 3 with a communication bore 7, which is preferably only 0.01 to 0.1 mm wide, to the capillary bore 3. The outwardly directed end of the communicating passage 5 is fitted with a tube connector 8 whereby the passage 5 can be connected to the measuring chamber (not shown).

In the installed state of the capillary element 1 the communicating passage 5 extends substantially obliquely from the upper part and normal to the capillary bore 3 so that any air bubbles which may be formed in the electrolyte in the region of the communicating passage 5 and its end cone 6 can rise and be carried away through the electrolyte inlet or outlet (not shown here) provided according to the invention on the measuring chamber. When a sample is sucked into the capillary bore 3 a small quantity of electrolyte fluid is also sucked in from passage 5 and end cone 6 through the very fine communication bore 7 whereby at the same time any very small air bubbles which may be present in this region are also carried away.

Figure 2:
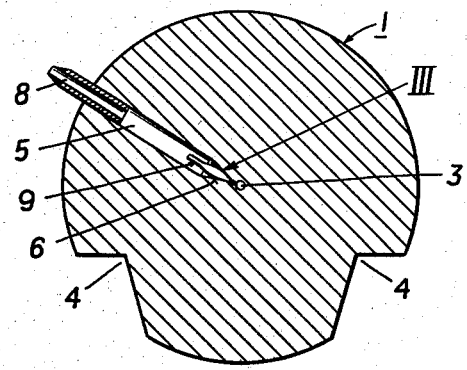
FIG. 2 is a cross section through another embodiment.
Figure 3:
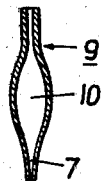
FIG. 3 shows detail III in FIG. 2.

The only difference between the capillary element 1 shown in FIG. 2 and that shown in FIG. 1 resides in that an additional nozzle tip 9, extruded from a polymer material, is inserted into the end cone 6 of the communicating passage 5. This nozzle tip 9 is secured in the communicating passage 5, preferably adhesively, adjacent to the capillary bore 3 and has a very fine communication bore 7, only 0.01 to 0.1 mm wide, to the capillary bore 3. FIG. 3 shows the nozzle tip 9 on a larger scale. It will be seen that there is a bulbous or pear-shaped enlargement 10 in the vicinity of the communication bore 7, which is formed very simply, for example by appropriately heating and at the same time stretching the polymer flexible tube material since with such materials this kind of treatment does not result in a cross sectional constriction but rather in the formation of the expansion bulb shown in the drawing.

The great advantage of the bulbous region 10 in the arrangement according to this invention resides in that it works as a mixing chamber and any particles of the test-sample which may have penetrated from the capillary bore 3 through the communication bore 7 are retained in this bulbous region 10. Since the volume of the bulbous 10 is no more than a few $\mu l$ the subsequent withdrawal of electrolyte from this region will always ensure that such impurities as well as the smallest air bubbles which may be present in the region of the communication bore 7 are carried away. If the nozzle tips are made of suitable polymer material such as polyethylene or polytetrafluorethylene, it is virtually impossible for any residual particles of the test sample to cling to the walls of the nozzle tip 9.

Figure 4:
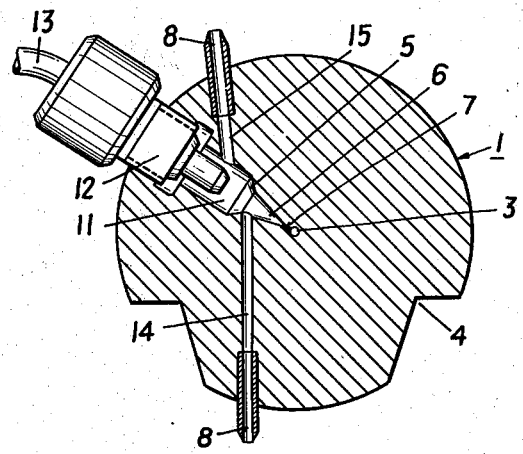
FIG. 4 shows another embodiment according to this invention.

FIG. 4 shows a reference electrode in which not only the communicating passage 5 with its end cone 6 and communication bore 7 but also the measuring chamber 11 itself, which is in communication with the capillary bore 3 through the electrolytic bridge established, are all formed in the capillary element 1. A suitable take-off electrode 12 preferably of the calomel or Ag/AgCl-type, is fitted in the measuring chamber 11 and connected by conductor 13 to associated electronic processing devices (not shown).

The measuring chamber 11 is connected to an electrolyte circuit (not specifically shown) in such a way that the electrolyte inlet 14 to the measuring chamber 11 is arranged at a point of said chamber 11 which is at a geometrically low position in the fitted state of the capillary element whilst the outlet 15 for the electrolyte is arranged at a geometrically high position of the measuring chamber 11. The electrolyte inlet 14 as well as the outlet 15 each comprise a tube connector 8 for their connection to the electrolyte circuit. This special arrangement of the electrolyte inlet and outlet of the measuring chamber 11, in combination with the advantages of the communicating passage 5 and the communication bore 7 to the capillary bore 3 already discussed with reference to the earlier described embodiments, prevents in a very simple manner the accumulation of air bubbles in the electrolytic bridge which would result in a distortion of the measured data.

Figure 5:
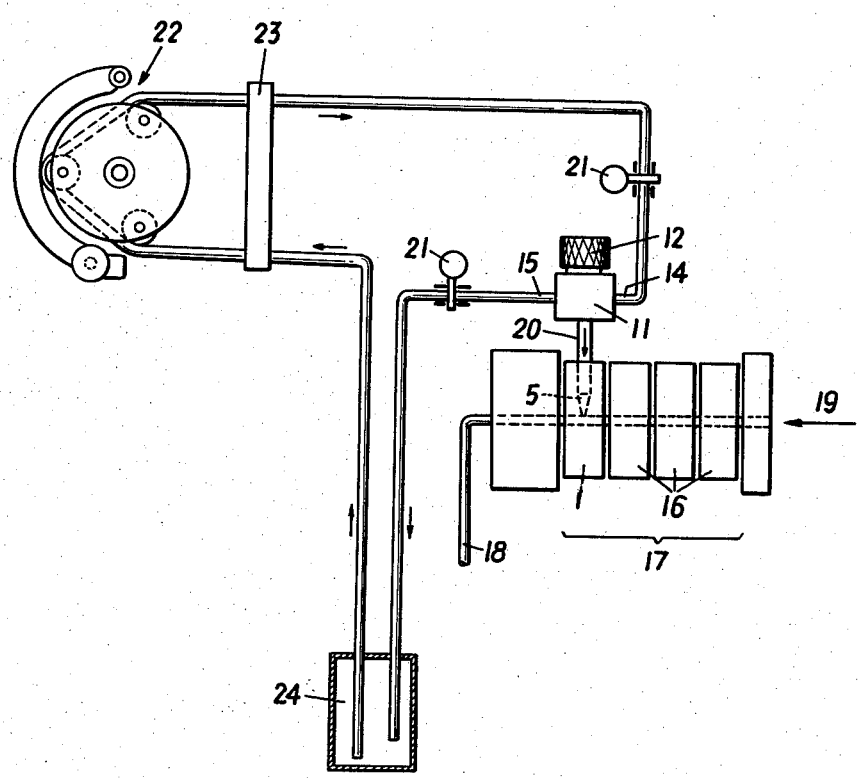
FIG. 5 illustrates a measuring system with a capillary reference electrode according to this invention.

The measuring system illustrated in FIG. 5 comprises a capillary reference electrode together with a capillary element 1 which is associated with further, similarly arranged electrodes, which may be sensitive, for example, to different ions, to form a measuring unit 17. The test sample which is to be tested is fed into this unit 17 in the direction of the arrow 19 by applying a partial vacuum or suction to flexible tube 18. In the illustrated example the measuring chamber 11 is arranged outside the capillary element 1 and connected thereto through a flexible tube 20 applied to the communicating passage 5 in the capillary element 1. The sensor electrode 12 is inserted into the measuring chamber 11 and suitably connected (not shown) to evaluator and processing equipment.

The measuring chamber 11 is further provided with an inlet 14 and an outlet 15 for the electrolyte circuit, the position of these connections being only schematically indicated in this figure.

The electrolyte circulation system, in which the electrolyte fluid circulates through resilient tubes, comprises two pinch valves 21 and a pump 22, to which the tubes are clamped fast by a connecting piece 23, as well as an electrolyte storage container 24.

Owing to the very low consumption in electrolyte fluid for each measuring operation which is achieved by the arrangement according to this invention, and also due to the provision of the electrolyte container, a large number of individual measuring operations may be carried out in automatic succession and the readings are significantly improved due to the elimination of air bubbles from the eletrolytic bridge, thus achieving a higher degree of measuring accuracy and reproduceability.

Figure 6:
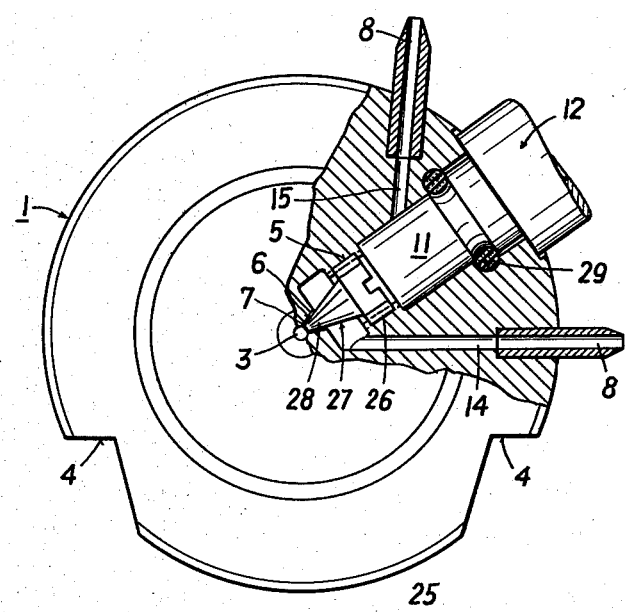
FIG. 6 is a cross section through another embodiment according to this invention.

According to a further development of the invention which is illustrated in FIG. 6, the capillary element 1 is substantially disc-shaped, comprising an axially through-extending capillary bore 3 and a centering or locating boss 25 which facilitates its connection to further, identical capillary elements. The underside of the capillary element 1 as shown in the drawing is provided with recesses or cut-outs 4 for easy concentric alignment and mutual securing of a plurality of such elements.

In order to form an electrolytic bridge between the capillary bore 3 and the measuring chamber 11, the latter being arranged within the element 1 in this particular embodiment of the invention, a communicating passage 5 is provided which has a substantially conical tip region 6 adjacent to the capillary bore 3. An insert element 27, likewise provided with a conical tip 28 in the region corresponding to tip 6 of passage 5 is detachably mounted in the communicating passage 5 by means of a screw thread 26.

An inlet 14 is provided in the lower region of communicating passage 5 and an outlet 15 is arranged in the upper region of the measuring chamber 11, both inlet and outlet having tube connectors 8 inserted from the outside of the capillary element 1. The electrolyte thus enters the measuring chamber 11 at a geometrically low point—considering the capillary element in its operational and fully fitted state—whilst leaving the chamber at a higher point, whereby the release of air bubbles which may occur in this region is effected in a very simple manner. A suitable electrode 12 is inserted into the upper side of the measuring chamber 11 and sealed by means of a sealing ring 29.

Figure 7:
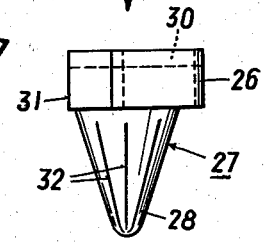
FIG. 7 is an enlarged view of the insert element shown in FIG. 6.
Figure 8:
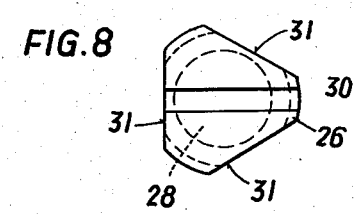
FIG. 8 is a view taken along arrow VIII in FIG. 7.

The conicity angle of the tip 28 of the insert element 27 is smaller than that of the conical end of communicating passage 5 so that the narrowest cross-section defined between insert element 27 and passage 5 lies at right angles to the axis of the insert element in the region of the junction of passage 5 and the capillary bore 3, where it forms the communication bore 7 (in this case annular) to the capillary bore 3. The cross section of this communication bore 7 can be easily varied by turning insert elements 27 in the screw thread 26 so that manufacturing and fitting tolerances can be very easily compensated. The rotation of insert element 27 is facilitated by a groove 30 provided in its upper side and shown particularly in FIGS. 7 and 8, for engagement by a screwdriver. FIGS. 7 and 8 also show flats 31 on the screw thread 26 of the insert element which preserve a clear cross-section in passage 5 also in the region of the screw thread 26.

If any obstruction should occur in the region of the communication bore 7 the insert element 27 can be very easily taken out to allow cleaning of the tip 28 of the insert element as well as of the narrow end 6 of the communicating passage 5. Besides, the annular configuration of the flow-passage ensures from the outset that there is very little risk of blocking for the extremely small cross-section of the communication bore.

FIG. 7 shows V-shaped grooves 32 extending longitudinally in the region of the conical tip 28 of the insert element 27 which arrangement would also permit the conical tip 28 to be a mating fit with the inside of tip 6 of the communicating passage 5 without completely obturating the communication bore 7 which, in that event, would consist only of a number of discrete passage-sections.

Finally it may be mentioned that instead of the flats 31 a variety of other technically equivalent provisions may be adopted, for example through-bores in the upper part of the insert element or in the region of the screw thread in the communicating passage, in order to preserve a clear flow cross-section through communicating passage 5 at all times.

We claim:

1. A capillary reference electrode, comprising a capillary body with a capillary bore, a chamber connected by an electrolytic bridge with a test sample capable of being introduced into said capillary bore, and a reference electrode extending into said chamber, the chamber being provided with an inlet and an outlet for charging said chamber with electrolyte, said inlet in the installed state of said capillary body, is arranged in a geometrically low position and said outlet at a geometrically high position on said chamber and for said electrolytic bridge is provided a communicating passage between said chamber and said capillary bore which communicating passage adjacent to said capillary bore has a substantially conical end with a communication bore to said capillary bore.

2. An electrode according to claim 1, wherein said communication bore has a clear flow section corresponding to a bore with a diameter in the range of 0.01 to 0.1 mm.

3. An electrode according to claim 1, wherein said chamber is arranged externally of said capillary body and said communicating passage has a flexible tube connector for its connection to said chamber.

4. An electrode according to claim 1, wherein said chamber as well as its inlet and outlet for the electrolyte is formed in the capillary body itself.

5. An electrode according to claims 1, 2, 3 or 4, wherein said communication bore to said capillary bore is formed in a nozzle tip drawn from a polymer material which is secured to the inside of said communicating passage next to said capillary bore and comprises a pear-shaped bubble in the vicinity of said communication bore.

6. An electrode according to claims 1, 2, 3 or 4, wherein a detachable insert element likewise comprising a substantially conical tip is arranged in the region of said conical tip of said communicating passage, and said communication bore to said capillary bore is defined between the tip of said insert element and the tip of said communicating passage.

7. An electrode according to claim 6, wherein the conicity angle of said tip of said insert element is less than the conicity angle of said tip of said communicating passage.

8. An electrode according to claim 6, wherein longitudinally extending V-grooves are formed in said conical tip of said insert element.

9. An electrode according to claim 6, wherein said insert element is adjustable in the axial direction relative to said tip of said communicating passage by means of a screw thread.

10. An electrode according to claim 4, comprising a capillary body which is constructed substantially disc-shaped, comprises an axially through-extending capillary bore and is adapted at its end faces for connection to further identical capillary bodies, wherein in the installed state of said capillary body, said communicating passage extends substantially obliquely from above and normally to said capillary bore.

11. A measuring system comprising a reference electrode according to claims 1, 2, 3 or 4, and an electrolyte-circuit connected to said inlet and outlet of said chamber, said circuit, besides comprising a pump, and shut-off valves upstream and downstream of said chamber also includes an electrolyte storage tank.

* * * * *